(12) United States Patent
Prodan et al.

(10) Patent No.: US 8,421,484 B2
(45) Date of Patent: Apr. 16, 2013

(54) DIELECTRIC SPECTROSCOPY ASSAYS FOR SCREENING OF ION CHANNEL LIGANDS

(75) Inventors: Camelia Prodan, Montclair, NJ (US); Victor I. Ilyin, Belle Mead, NJ (US); Donald J. Kyle, Newton, PA (US); Kevin Carlin, Hamilton, NJ (US); Gang Wu, Princeton, NJ (US)

(73) Assignees: Purdue Pharma L.P., Stamford, CT (US); New Jersey Institute of Technology, Newark, NJ (US)

( * ) Notice: Subject to any disclaimer, the term of this patent is extended or adjusted under 35 U.S.C. 154(b) by 421 days.

(21) Appl. No.: 12/671,309

(22) PCT Filed: Jul. 30, 2008

(86) PCT No.: PCT/US2008/071645
§ 371 (c)(1), (2), (4) Date: Jun. 21, 2010

(87) PCT Pub. No.: WO2009/018379
PCT Pub. Date: Feb. 5, 2009

(65) Prior Publication Data
US 2010/0259286 A1 Oct. 14, 2010

Related U.S. Application Data

(60) Provisional application No. 60/953,179, filed on Jul. 31, 2007.

(51) Int. Cl.
*G01R 27/08* (2006.01)
(52) U.S. Cl.
USPC .................................. 324/692; 435/4; 702/19

(58) Field of Classification Search .......... 324/200–232, 324/693, 692; 204/403.01, 403.06, 403.07; 205/775, 778, 792; 702/19, 21
See application file for complete search history.

(56) References Cited

U.S. PATENT DOCUMENTS

| | | | |
|---|---|---|---|
| 4,348,107 A | 9/1982 | Leif | |
| 2006/0136140 A1* | 6/2006 | Perschke et al. | 702/19 |
| 2007/0128653 A1* | 6/2007 | Jegla | 435/6 |

OTHER PUBLICATIONS

Cellular Dielectric Spectroscopy: A label-Free Technology for Drug Discovery; Gordo Leung, Roger Tang, Ryan McGuinness, Edward Verdonk, Julia Michelotti and Vivian Liu; Journal of Laboratory Automation 2005 10: 258; Aug. 1, 2005.*
Dielectric spectroscopy of single cells: time domain analysis using Maxwell's mixture equation; Tao Sun, Shady Gaward, Nicolas Green and Hywel Morgan; Dec. 15, 2006.*
Bergman, "Bounds for the complex dielectric constant of a two-component composite material," *Physical review B*, vol. 23, No. 6, pp. 3058-3065 (1981).
Bordi et al., "Reduction of the contribution of electrode polarization effects in the radiowave dielectric measurements of highly conductive biological cell suspensions," *Bioeletrochemistry*, vol. 54, pp. 53-61 (2001).
Cheung et al., "Impedance Spectroscopy Flow Cytometry: On-Chip Label-Free Cell Differentiation," *Cytometry Part A*, vol. 65A, pp. 124-132 (2005).

(Continued)

*Primary Examiner* — Melissa Koval
*Assistant Examiner* — Feba Pothen
(74) *Attorney, Agent, or Firm* — Troutman Sanders LLP

(57) ABSTRACT

A method for measuring membrane potential using dielectric spectroscopy is described. A new theoretical model allows for the determination of membrane potential from low-frequency impedance measurements to provide a non-evasive method which is both rapid and inexpensive.

22 Claims, 5 Drawing Sheets

OTHER PUBLICATIONS

Foster et al., "Dielectric Properties of Tissues and Biological Materials: A Critical Review," *Critical Reviews in Biomedical Engineering*, vol. 17, Issue 1, pp. 25-104 (1989).

Gawad et al., "Dielectric spectroscopy in a micromachined flow cytometer: theoretical and practical considerations," *Miniaturisation for Chemistry, biology & Bioengineering*, vol. 4, pp. 241-251 (2004).

Gheorghiu, "Measuring living cells using dielectric spectroscopy," *Bioelectrochemistry and Bioenergetics*, vol. 40, pp. 133-139 (1996).

Gheorghiu et al., Characterizing Cellular Systems by Means of Dielectric Spectroscopy, *Bioelectromagnetics*, vol. 17, pp. 475-482 (1996).

Lichtshtein et al., "Use of a lipophilic cation for determination of membrane potential in neuroblastoma-glioma hybrid cell suspensions," *Proc. Natl. Acad. Sci.*, vol. 76, No. 2, pp. 650-654 (1979).

Prodan et al., "The dielectric behaviour of living cell suspensions," *J. Phys. D: Appl. Phys.*, vol. 32, pp. 335-343 (1999).

Prodan et al., "Low-frequency, low-field dielectric spectroscopy of living cell suspensions," *Journal of applied Physics*, vol. 95, No. 7, pp. 3754-3756 (2004).

Prodan et al., "The dielectric behavior of the living cell suspensions," *J. Physics D: Applied Physics*, vol. 32, No. 3, pp. 335-343 (1-16) (1999).

Rall et al., "Space-Clamp Problems When Voltage Clamping Branched Neurons with Intracellular Microelectrodes," *American Physiological Society*, Bethesda, Maryland, pp. 191-214.

Roepe et al., "Lower Electrical Membrane Potential and Altered pHi Homeostasis in Multidrug-Resistant (MDR) Cells Further Characterization of a Series of MDR Cell Lines Expressing Different Levels of P-Glycoprotein," *biochemistry*, vol. 32, pp. 11042-11056 (1993).

Shilov et al., *Kolloidn. Zh.*, vol. 32, pp. 293-300 (1970)—not in English.

Sims et al., Studies on the Mechanism by Which Cyanine Dyes Measure Membrane Potential in Red Blood Cells and Phosphatidylcholine Vesicles, *Cyanine Dyes as Membrane Potential Probes, Biochemistry*, vol. 13, No. 16, pp. 3315-3330 (1974).

Stoy et al., Dielectric properties of mammalian tissues from 0.1 to 100 MHz: a summary of recent data, *Phys. Med. Biol.*, vol. 27, No. 4, pp. 501-513 (1982).

Uechi et al., Stability of membrane potential in heart mitochondria: Single mitochondrion imaging, *Biochemical and biophysical Research Communications*, vol. 344, pp. 1094-1101 (2006).

Vergun et al., Fluctuations in Itochondrial Membrane Potential in Single Isolated Brain Mitochondria: Modulation by Adenine Nucleotides and $Ca^{2+}$, *Biophysical Journal*, vol. 87, pp. 3585-3593 (2004).

Vrinceanu et al., "Shape effects on the dielectric behaviour of arbitrarily shaped particles with particular reference to biological cells," *Bioelectrochemistry and bioenergetics*, vol. 40, pp. 167-170 (1996).

Wright, "Generation of resting membrane potential," *Adv. Physiol. Educ.*, vol. 28, pp. 139-142 (2004).

* cited by examiner

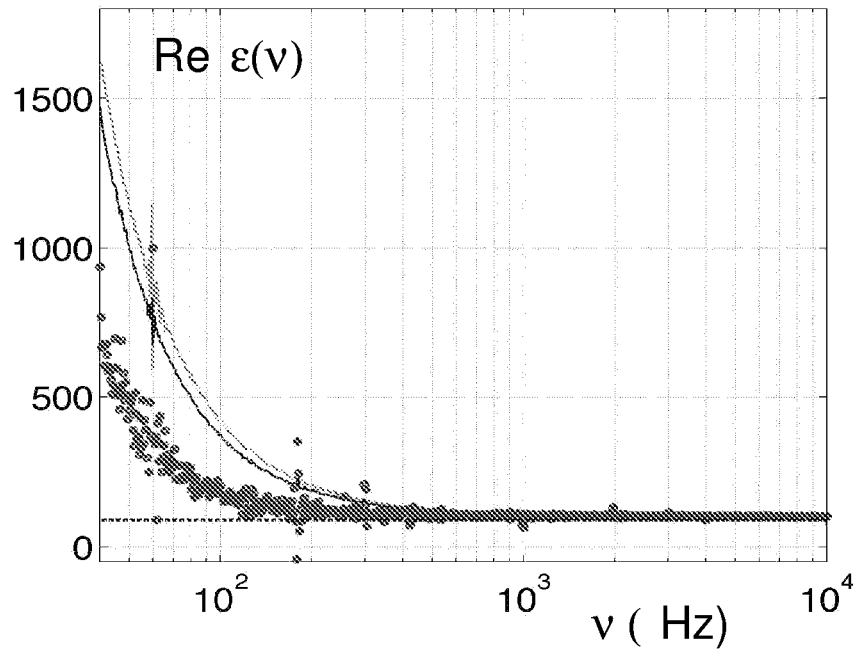
Figure 3
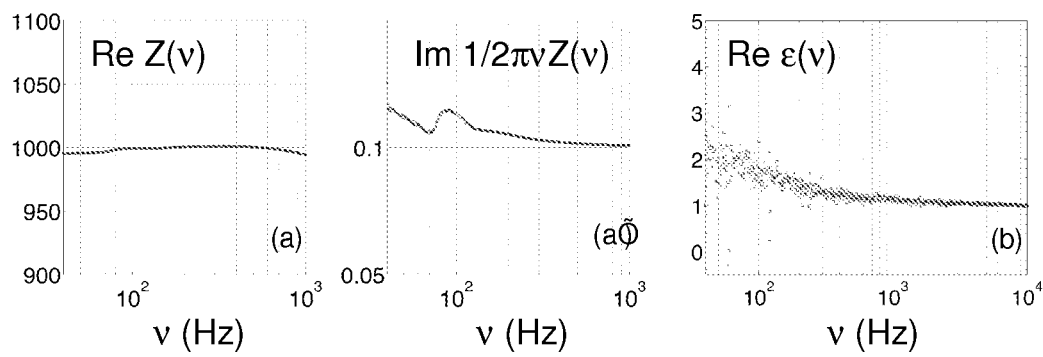
Figures 4(a), 4(a') and 4(b)

$IC_{50} = 2.46\ \mu M$
Slope = 1.03

DIELECTRIC SPECTROSCOPY ASSAYS FOR SCREENING OF ION CHANNEL LIGANDS

This application claims priority under 35 U.S.C. §119(e) to U.S. Provisional Patent Application Ser. No. 60/953,179 filed Jul. 31, 2007. This application is incorporated herein by reference in its entirety.

FIELD OF THE INVENTION

The present invention relates generally to methods for measuring membrane potentials of living mammalian cells using dielectric spectroscopy.

BACKGROUND OF THE INVENTION

Finding new drugs which have specific modulatory effects on ion channels requires methods for measuring and manipulating the membrane potential of cells with the ion channels present in the membrane. A number of methods exist today that can be used to measure cell transmembrane potentials and to measure the activities of specific ion channels. Probably the best known approach is the patch clamp, originally developed by Neher, Sakmann, and Steinback. (The Extracellular Patch Clamp, A Method For Resolving Currents Through Individual Open Channels In Biological Membranes", *Pfluegers Arch.* 375; 219-278, 1978; Hamill et al. Improved patch-clamp techniques for high-resolution current recording from cells and cell-free membrane patches. *Pflugers Arch.* 391(2); 85-100, (1981)). Other methods include optical recording of voltage-sensitive dyes or proteins (Cohen et al., *Annual Reviews of Neuroscience* 1:171-82, 1978), extracellular recording of fast events using metal (Thomas et al., *Exp. Cell Res.* 74:61-66, 1972) or field effect transistors (FET) (Fromherz et al., *Science* 252:1290-1293, 1991) electrodes, or by modulating the transmembrane potential with applied electric fields and the measurement of this change using fluorescent dyes (U.S. Pat. No. 6,686,193). Still other methods include using extracellular electrodes (Thomas et al., *Exp. Cell Res.* 74:61-66, 1972), radioactive flux assays, the expression of endogenous proteins or the use of reporter genes or molecules.

The patch clamp technique is significantly limited by its low throughput. Further, it is not easily amenable to automation. Similarly, optical detection systems are limiting in that they require the use of one or more dyes and do not provide the ability to regulate, or clamp, the transmembrane potential of a cell during the measurement.

Dielectric spectroscopy (DS) can be used to study the electrical properties of living cell suspensions. There has been significant interest over the time in measuring the complex dielectric function of cells in suspensions. There are several dielectric spectroscopy techniques that have been applied directly to biological systems (See G. R. Facer, et al., *Appl. Phys. Lett.* 78 (2001), no. 7, 996-998; H. E. Ayliffe, et al., *J. Microelectromechanical Systems* 8 (1999), no. 1, 50-56; G. De Gasperis, et al, *Measurement Science and Technology* 9 (1998), no. 3, 518-529; G. Smith, et al., *J. Pharmaceutical Sciences* 84 (1995), no. 9, 1029-1044; E. Gheorghiu, *Bioelectrochemistry and Bioenergetics* 40 (1996), no. 2, 133-139; and E. Gheorghiu and K. Asami, *Bioelectrochemistry and Bioenergetics* 45 (1998), no. 2, 139-143). However, most either become non-reliable in the low frequency range or involve extremely large electric fields.

The frequency dependent permittivity and/or conductivity of a material or a living organism has been measured using linear dielectric spectroscopy. (See S. Gawad, K. Cheung, U. Seger et al., Dielectric spectroscopy in a micromachined flow cytometer: theoretical and practical considerations, *Lab on a Chip* 4 (2004), 241-251; and E. Gheorghiu, Measuring living cells using dielectric spectroscopy, *Bioelectrochemistry* 40 (1996), 133-139). However, dielectric spectroscopy has not been shown to be useful for measuring membrane potential of mammalian cells, particularly in a screening or high throughput assay.

For the low frequency range the alpha dispersions are known to provide information on cell behavior by observing the evolution of electrical and morphological parameters during cell cycle progressions. This data has theoretically known to provide information on the transmembrane potential of the cell (Gheorghiu (1996). Characterizing cellular systems by means of dielectric spectroscopy. *Bioelectromagnetics* 17:475-482). (C. Prodan and E. Prodan (1999), The Dielectric Behavior of Living Cell Suspensions, *J. Phys. D: Appl. Phys.* 32 335-343). However, the theory has not been sufficient to accurately and quickly calculate the membrane potential until now.

SUMMARY OF THE INVENTION

The present invention provides new and novel methods for measuring a change in membrane potential in mammalian cell having an ion channel. In one embodiment, the method comprises: (a) measuring the resting impedance in the alpha dispersion frequency range of a mammalian cell having the ion channel; (b) exposing a mammalian cell having the ion channel of the cell of step (a) to a test agent; (c) measuring the impedance in the alpha dispersion frequency range of the cell of step (b); and (d) calculating the change in the membrane potential of the cell upon exposure to the test agent, wherein calculating comprises:

(i) determining the shape of the cell; and (ii) determining the change in the membrane potential based on fitting the measured impedance with the theoretical model wherein:

$$\varepsilon_{sus}(\omega) = \varepsilon_0^* \left(1 + \frac{p\alpha(\omega)}{1 - p\alpha(\omega)/3}\right),$$

$$\text{with } \overline{\alpha}(\omega) = \frac{1}{VE_0} \int_V dV \frac{\varepsilon^* - \varepsilon_0^*}{\varepsilon_0^*} \langle \overline{E}(\omega) \rangle,$$

wherein $\in_0^*$ is the complex dielectric function of the medium, p is the volume concentration of the solution, $\alpha(\omega)$ is the frequency dependent polarizability, V is the volume, $\overline{E}_0$ electric field of amplitude, $\in^*$ is the non-uniform complex dielectric function of the composite particle, and $\overline{E}(\omega)$ is the electric field inside the particle.

Each of the parameters are discussed herein below. Each of p, $\in_1^*$, and $\sigma_0$ can be obtained from literature values or from experimental measurements. Parameters other than polarizability ($\alpha$) and the membrane potential ($\Delta V_0$, which is set by the ratio $\gamma/D$) can be obtained from the literature or calculated from the experiment (cell concentration), from a separate experiment such as light microscopy to measure the size and shape of the cells.

In one embodiment, polarization effect is removed from the impedance data.

In another embodiment, the cell is placed in a microfluidic system and flowed through a chamber.

In one embodiment, the mammalian cell used to measure the resting impedance is a different cell than the cell used to measure the impedance of the cell exposed to the test agent.

In one embodiment, the mammalian cell used to measure the resting impedance is the same cell used to measure the impedance of the cell exposed to the test agent.

In one embodiment, the cell is exposed to at least one different concentration of test agent and at least one additional impedance measurement is subsequently obtained.

In one embodiment, the method further comprising washing out the test agent, adding a second test agent, and measuring the impedance in the alpha dispersion frequency range of the cell after exposure to the second test agent.

In one embodiment, each impedance measurement is obtained from 1 Hz to 10 KHz. In another embodiment, each impedance measurement is obtained from 100 to 1000 Hz.

In one embodiment, the method further comprising accepting or rejecting or accepting the test agent based on the calculated change in membrane potential.

In one embodiment, the ion channel is a hERG channel.

In one embodiment, the method further comprising the step of adding an ion channel antagonist after measuring the cell's resting impedance.

In one embodiment, the ion channel antagonist is quinidine. In another embodiment, the ion channel antagonist is selected from quinidine, propanolol, and astemizole. In another embodiment, the ion channel antagonist is an antiarrhythmic agent (e.g., disopyramide, procainamide, quinidine, lidocaine, phenyloin, flecamide, propafenone, propranolol, timolol, metoprolol, sotalol, atenolol, amiodarone, sotalol, bretylium, nibentan, dofetilide, verapamil, or diltiazem) or an antihistamine with cardiac side effects (e.g., astemizole or terfenadine).

In one embodiment, a plurality of cells is measured simultaneously.

In one embodiment, the test agent is a modulator of ion channel activity. In another embodiment, the method, further comprising the step of calculating the $IC_{50}$ value of the test agent.

In one embodiment, the cell is a mammalian cell containing a hERG ion channel

In one embodiment, the ion channel has a resting potential of less than 0 V.

Yet another embodiment of the present invention provides a method for measuring change in membrane potential in a cell containing a hERG ion channel comprising: (a) measuring the impedance of a mammalian cell having an ion channel in the alpha dispersion frequency range within a chamber; (b) combining a test agent and the mammalian cell having an ion channel; (c) measuring the impedance of the combination from step (b) in the alpha dispersion frequency range; and (d) calculating the change in the membrane potential of the cell, wherein calculating comprises: determining the change in the membrane potential based on fitting the measured impedance with the theoretical model wherein:

$$\varepsilon_{sus}(\omega) = \varepsilon_0^*\left(1 + \frac{p\alpha(\omega)}{1 - p\alpha(\omega)/3}\right),$$

$$\text{with } \bar{\alpha}(\omega) = \frac{1}{VE_0}\int_V dV \frac{\varepsilon^* - \varepsilon_0^*}{\varepsilon_0^*}\langle \bar{E}(\omega)\rangle,$$

wherein $\alpha(\omega)$ is defined for a spherical shape, wherein $$\alpha(\omega) = \frac{6\lambda_1}{3-\lambda_1}\left[1 - \frac{2R\gamma/D}{\left(1 + j\omega\frac{R^2}{2D}\right)(3-\lambda_1)(\tilde{\varepsilon}_1^* + \varepsilon_0^*) + 2R\gamma/D}\right],$$

Each of the parameters are discussed herein below. R is the radius, γ is the conductivity of the bound charges (γ=uρ), u is the mobility constant, and D is the diffusion constant of the bound charge. Parameters other than polarizability (α) and the membrane potential ($\Delta V_0$, which is set by the ratio γ/D) can be obtained from the literature or calculated from the experiment (cell concentration), from a separate experiment such as light microscopy to measure the size and shape of the cells. Each of p, $\lambda_1$, $\tilde{\in}^*_1$, d, R, $\in_1$, $\in_2$, $\sigma_2$, u, $\in_0$, $\sigma_0$ can be obtained from the literature values or from experimental measurements, and the membrane potential $\Delta V_0$ is defined by the ratio γ/D.

Yet another embodiment of the present invention provides a method of screening a library of compounds for a channel modulator comprising: (a) measuring the resting impedance in the alpha dispersion frequency range of a mammalian cell having the ion channel; (b) exposing a mammalian cell having the ion channel of the cell of step (a) to a test agent; (c) measuring the impedance in the alpha dispersion frequency range of the cell of step (b); and (d) calculating the change in the membrane potential of the cell upon exposure to the test agent, wherein calculating comprises:
 (i) determining the shape of the cell; and
 (ii) determining the change in the membrane potential based on fitting the measured impedance with the theoretical model wherein:

$$\varepsilon_{sus}(\omega) = \varepsilon_0^*\left(1 + \frac{p\alpha(\omega)}{1 - p\alpha(\omega)/3}\right),$$

$$\text{with } \bar{\alpha}(\omega) = \frac{1}{VE_0}\int_V dV \frac{\varepsilon^* - \varepsilon_0^*}{\varepsilon_0^*}\langle \bar{E}(\omega)\rangle.$$

Each of p, $\tilde{\in}^*_1$, and $\sigma_0$ can be obtained from literature values or from experimental measurements.

In one embodiment, the method further comprises screening the compounds for activity in a plurality of ion channels.

In one embodiment, a polarization effect is removed from the impedance data.

In one embodiment, the cell is placed in a microfluidic system and flowed through a chamber.

In one embodiment, the mammalian cell used to measure the resting impedance is a different cell than the cell used to measure the impedance of the cell exposed to the test agent.

In one embodiment, the mammalian cell used to measure the resting impedance is the same cell used to measure the impedance of the cell exposed to the test agent.

In one embodiment, the cell is exposed to at least one different concentration of test agent and at least one additional impedance measurement is subsequently obtained.

In one embodiment, the method further comprising washing out the test agent, adding a second test agent, and measuring the impedance in the alpha dispersion frequency range of the cell after exposure to the second test agent.

In one embodiment, each impedance measurement is obtained from 1 Hz to 10 KHz. In another embodiment, each impedance measurement is obtained from 100 to 1000 Hz.

In one embodiment, the method further comprising accepting or rejecting or accepting the test agent based on the calculated change in membrane potential.

In one embodiment, the ion channel is a hERG channel.

In one embodiment, the method further comprising the step of adding an ion channel antagonist after measuring the cell's resting impedance. For example, the ion channel antagonist may be quinidine In one embodiment, a plurality of cells is measured simultaneously.

In one embodiment, the test agent is a modulator of ion channel activity.

In one embodiment, the method further comprises the step of calculating the $IC_{50}$ value of the test agent.

In one embodiment, the cell is a mammalian cell containing a hERG ion channel

In one embodiment, the ion channel has a resting potential of less than 0 V.

Yet another embodiment of the present invention provides a method of selecting a modulator of an ion channel comprising: placing a mammalian cell containing an ion channel in a chamber having two electrodes (a) measuring the resting impedance in the alpha dispersion frequency range of a mammalian cell having the ion channel; (b) exposing a mammalian cell having the ion channel of the cell of step (a) to a test agent; (c) measuring the impedance in the alpha dispersion frequency range of the cell of step (b); and (d) calculating the change in the membrane potential of the cell upon exposure to the test agent, wherein calculating comprises:
 (i) determining the shape of the cell; and
 (ii) determining the change in membrane potential based on fitting the measured impedance with the theoretical model wherein:

$$\varepsilon_{sus}(\omega) = \varepsilon_0^* \left(1 + \frac{p\alpha(\omega)}{1 - p\alpha(\omega)/3}\right),$$

$$\text{with } \bar{\alpha}(\omega) = \frac{1}{VE_0} \int_V dV \frac{\varepsilon^* - \varepsilon_0^*}{\varepsilon_0^*} \langle \bar{E}(\omega) \rangle.$$

Each of p, $\tilde{\varepsilon}^*_1$, and $\sigma_0$ can be obtained from literature values or from experimental measurements, wherein said test agent is selected as a modulator of an ion channel if said agent changes the membrane potential.

Yet another embodiment of the present invention provides a high-throughput screening system comprising: a plurality of chambers having two electrodes in each of the plurality of chambers, wherein the electrodes are configured to applies a series of electric fields to cells within the chambers; a means for flowing solutions or suspensions containing mammalian cells containing an ion channel into and out of the chamber; a dielectric spectrometer configured to obtain impedance measurements in the alpha dispersion region; a data processing unit configured to calculating the membrane potential from impedance data, wherein calculating comprises:
 determining the shape of the cell,
 determining the membrane potential based on fitting the measured impedance with the theoretical model wherein:

$$\varepsilon_{sus}(\omega) = \varepsilon_0^* \left(1 + \frac{p\alpha(\omega)}{1 - p\alpha(\omega)/3}\right),$$

$$\text{with } \bar{\alpha}(\omega) = \frac{1}{VE_0} \int_V dV \frac{\varepsilon^* - \varepsilon_0^*}{\varepsilon_0^*} \langle \bar{E}(\omega) \rangle.$$

Each of p, $\tilde{\varepsilon}^*_1$, and $\sigma_0$ can be obtained from literature values or from experimental measurements.

Other features, advantages and embodiments of the invention will be apparent to those skilled in the art from the following description, accompanying data and appended claims.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

FIG. 1(a) Experimental setup for one embodiment of the invention. FIG. 1(b) shows the electronic circuitry for one aspect of the invention.

FIG. 3. Relative permittivity as computed from the measured impedance without any post-processing. The two lines correspond to d1=9 mm and d2=10 mm. The points represent the relative permittivity computed using the distance variation technique formula.

FIGS. 4(a), 4(a'), and 4(b). FIG. 4(a) Real part of Z in ohms. FIG. 4(a') The measured capacitance in μF. FIGS. (a) and (a') refer to the case when the probe was replaced by a parallel RC circuit with R=1000μ, and C=0.1 μF (10% accurate). FIG. 4(b) Measured relative dielectric permittivity when the probe is kept in the air. No post-data processing was used.

FIG. 6(a) Patch clamp measurements with increasing concentrations of quinidine in solution. FIG. 6(b) Percent inhibition compared to quinidine concentration and $IC_{50}$ values.

FIG. 7(a) quinidine. FIG. 7(b) propanolol. FIG. 7(c) astemizole.

DETAILED DESCRIPTION OF PREFERRED EMBODIMENTS

Figures 1A, 1B:
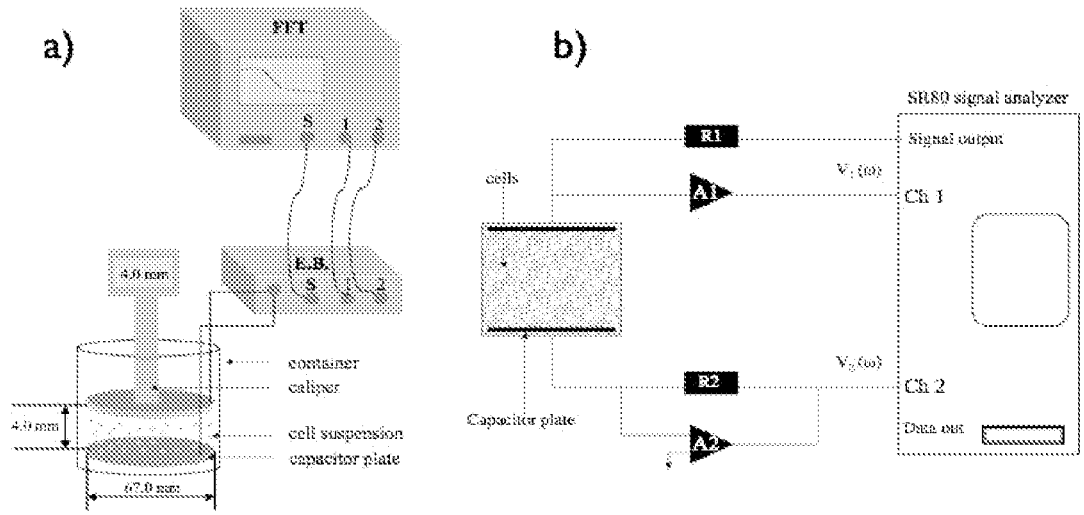
FIGS. 1(a)-1(b).

Due to the fact that ion channels are capable of conducting ions between the intracellular and extracellular compartments, opening or closing of these protein channels results in transmembrane potential changes. These potential changes are either depolarizing or hyperpolarizing depending on the particular assay and ion selectivity of the channel involved. Therefore, compounds that interact with the expressed ion channel and alter the membrane potential are detected by dielectric permittivity measurements of the cell. The present invention provides fast and accurate measurements of changes in membrane potential.

Definitions

The following definitions are set forth to illustrate and define the meaning and scope of the various terms used to describe the invention herein.

As used herein, the phrase "accepting or rejecting" means that a decision whether to keep the test compound for further analysis and testing or reject the compound as inappropriate or non-useful is made based on one or more predetermined parameters. (i.e. all compounds blocking the hERG channel are rejected from a test for active drug agents.

The term "activation" refers to the transition from a resting (non-conducting) state of an ion channel to the activated (conducting) state.

The term "alpha dispersion" (or "α-dispersion," or "α-plateau") is a result of concentration polarization of the electric double layer Shilov, V. N., and S. S. Dukhin. 1970. *Kolloidn. Zh.* 32:293-300. Alpha dispersions appear from 100 Hz to 10 KHz (Gheorghiu, 1996, *Bioelectromagnetics* 17:475-482). Alpha dispersion information enables the evaluation of the biological cell resting potential and cell morphology, while information on the permittivity and the conductivity of cellular subcompartments—for example the cell membrane, the cytoplasm—are revealed in the β-dispersions range.

The term "anode" refers to an electrode when driven to a positive potential relative to earth by an external source.

The term "capacitor," as used here, includes a chamber wherein two electrodes sandwiching a dielectric material, such as a solution containing cells. A capacitance value of the capacitor characterizes an amount of charge that would be collected at the electrodes for a given applied voltage between the electrodes. This capacitance value is expressed by the equation:

$$C = \in_{r \in .sub.o} A/d$$

wherein $\in_r$=the relative dielectric constant of the suspended or adherent cells situated between electrodes, $\in_0$=the permittivity of free space, A=the surface area of the electrodes, and d=the distance between the electrodes. Thus, the capacitance value (C) of the capacitor is directly proportional to an area (A) of opposing surfaces of the electrodes, directly proportional to a relative dielectric constant ($\in_r$) of the dielectric, and inversely proportional to the distance (d) between the electrodes.

The term "cathode" refers to an electrode when driven to a negative potential relative to earth by an external source.

The term "chamber" includes a volume, such as a cuvette, beaker, single well of a 96-multiwell plate, centrifuge tube, or a portion of the interior of a tube such as a flow injection tube. The chamber used for DS measurements, also includes two electrodes. Preferably, the chamber and electrodes are a good approximation of an ideal capacitor.

The term "depolarize" means to cause the transmembrane potential of a cell to become closer to zero. In the case of cells that are normally at negative resting potentials, this term means that the transmembrane potential changes in a positive direction.

The phrase "dielectric spectroscopy," or DS, is spectroscopy measures the dielectric properties of a medium as a function of frequency. The measurements are based on the interaction of an external field with the electric dipole moment of the sample.

The term "electrode" means a controllable conductive interface between an instrument and a test system.

The term "hyperpolarize" means to cause the transmembrane potential of a cell to move farther away from zero. In the case of cells that are normally at negative resting potentials, this term means that the transmembrane potential changes in a negative direction.

The phrase "ideal capacitor" means a capacitor that, once charged by a given applied voltage, holds the collected charge for an infinite duration—i.e., permitting no leakage current through the dielectric between the electrodes. Such ideal capacitor would also tolerate large voltage applications. However, it is known that certain physical limitations of real-world materials restrict the availability of such an ideal capacitor.

The phrase "ion channel antagonist" refers to compounds that binds to an allosteric site on the receptor or an associated ion channel and blocks, prevents, or nullifies a pharmacological response. Other types of antagonism are competitive where the antagonist attenuates the effects of an agonist.

The phrase "ion channel agonist" refers to a compound that binds to the ion channel and activates it, producing a pharmacological response.

The phrase "ion channel blocker" refers to compounds that block or obstruct the ion channel.

The phrase "multiwell plate" refers to a two dimensional array of addressable wells located on a substantially flat surface. Multiwell plates may comprise any number of discrete addressable wells, and comprise addressable wells of any width or depth. Common examples of multiwell plates include 96 well plates, 384 well plates and 3456 well Nanoplates™.

The phrase "transmembrane potential modulator" refers to components capable of altering the resting or stimulated transmembrane potential of a cellular or sub-cellular compartment. The term includes discrete compounds, receptors, pore forming proteins, or any combination of these components. Examples of transmembrane potential modulators included activation (moving from a resting to the open state), deactivation (moving from the open state to a resting state), inactivation (moving from a resting or open state to an inactivated state), release from inactivation (moving from an inactivated state to a resting state), and flickering (moving from an inactivated state to the open state).

The phrase "test agent" or test compound refers to a chemical to be tested by one or more screening method(s) of the invention as a putative ion channel modulator. A test compound can be any chemical, such as an inorganic chemical, an organic chemical, a protein, a peptide, a carbohydrate, a lipid, or a combination thereof. Usually, various predetermined concentrations of test compounds are used for screening, such as 0.001 μM, 0.003 μM, 0.01 μM, 0.03 μM, 0.1 μM, 0.3 μm, 1 μM, 3 μM, and 10 μM. Test compound controls can include the measurement of the impedance in the absence of the test compound or comparison to a compound known to modulate the target. For example, quinidine can be used as a known modulator which blocks the hERG potassium ion channel.

The terms "transfected" refers to a cell into which (or into an ancestor of which) has been introduced, by means of recombinant nucleic acid techniques, a heterologous nucleic acid molecule.

Following long-standing patent law convention, the terms "a" and "an" mean "one or more" when used in this specification and claims.

Generally, the nomenclature used herein and many of computer, detection, chemistry, fluidics, and laboratory procedures described below are those well known and commonly employed in the art. Standard techniques are usually used for chemical synthesis, electrode fabrication and use, microfluidics, molecular biology, computer software and integration. Generally, chemical reactions, cell assays and enzymatic reactions are performed according to the manufacturer's specifications where appropriate. The techniques and procedures are generally performed according to conventional methods in the art and various general references, including those listed below, which are herein incorporated by reference. Sambrook et al. *Molecular Cloning: A Laboratory Manual*, 3$^{rd}$ ed. (2001) Cold Spring Harbor Laboratory Press, Cold Spring Harbor, N.Y., for molecular biology methods; Cells: *A Laboratory Manual*, 1$^{St}$ edition (1998) Cold Spring Harbor Laboratory Press, Cold Spring Harbor, N.Y., for cell biology methods; Hille, B. *Ionic Channels of Excitable membranes*, Third Edition (2001) Sinauer Associates, Inc., Sunderland, Mass. for general electrophysiological methods and properties of ion channels. Horowitz and Hill, *The Art of Electronics*, Second Edition (1989) Cambridge University Press, Cambridge, U.K. for electronic circuits.

Dielectric Behavior of Living Cells

Cellular membrane potential is the electrical potential difference (i.e., voltage) across the plasma membrane. The membrane potential is also referred to as the transmembrane potential, transmembrane potential difference, and transmembrane potential gradient. Membrane potential arises from the action of ion transporters which are embedded in the membrane and maintain viable ion concentrations inside the cell. Typically, the membrane potential arises from the separation of ions (i.e., $Ka^+$, $Na^+$, $Ca^{2+}$ or $Cl^-$) from intracellular immobile anions across the membrane of the cell.

The dielectric response of live cells is fundamentally different from that of dead cells (S. Wright, Generation of resting membrane potential, *Adv. Physiol Educ* 28 (2004), 139; H. R. K. D. Lichtshtein, A. J. Blume, Use of lipophilic cation for determination of membrane potential in neuroblastoma-glycoma hybrid cell suspensions, *Proc. Natl. Acad. Sc U.S.A.i.* 76 (1979), no. 2, 650). From the dielectric point of view, the main difference is the existence of the membrane potential in live cells. In what concerns the dielectric response, the main effect of the membrane potential is the accumulation of free electric charges at the membrane surfaces. The concentration of the charges is directly related to the magnitude of the membrane potential (J. T. G. S. et. al, Voltage and patch clamping with microelectrodes, Williams and Wilkins, Baltimore, 1985). When the cells are placed in time oscillating electric fields, these charges move on the surface of the membrane, giving rise to extremely high polarizabilities or to the alpha plateau, where live cells display very strong dielectric responses. Since the mobility of charges on the membrane surface is relatively small, this effect appears only at low frequencies, typically below 100 kHz. In this range of frequencies, the relative dielectric permittivity of live cell suspensions can be as high as $10^6$ (J. S. et. al, *Methods in membrane and transporter research*, R. G. Landes Company, Austin, 1994; H. Lodish, *Molecular cell biology*, W. H. Freeman, New York, 2000; P. J. S. e. al, Studies on the mechanism by which cyanine dyes measure membrane potential in red blood cells amd phosphatidylcholine vesicles, *Biochemistry* 13 (1974), no. 16, 3315). Quantification is described by T. Brody (*Nutritional biochemistry*, Academic Press, San Diego, 1999). Others have used the spectral decomposition method originally proposed by Bergman and variations thereof (K. R. Foster and H. P. Schwan, Dielectric properties of tissues and biological materials: A critical review, *Critical Reviews in Biomedical Engineering* 17 (1989), no. 1, 25-104; P. D. Roepe, W. Li Yong, J. Cruz and D. Carlson, Lower electrical membrane potential and altered ph(i) homeostasis in multidrug-resistant (mdr) cells: Further characterization of a series of mdr cell lines expressing different levels of p-glycoprotein, *Biochemistry* 32 (1993), no. 41, 11042-11056; Y. Uechi, H. Yoshioka, D. Morikawa and Y. Ohta, *Stability of membrane potential in heart mitochondria: Single mitochondrion imaging*, Biochemical and Biophysical Research Communications 344 (2006), no. 4, 1094-1101; and O. Vergun and I. J. Reynolds, Fluctuations in mitochondrial membrane potential in single isolated brain mitochondria: Modulation by adenine nucleotides and ca2+, *Biophysical Journal* 87 (2004), no. 5, 3585-3593)

The presence of the membrane potential has a specific effect on the dielectric behavior of cell suspensions, namely the appearance of the alpha dispersion in the low frequency part of the dielectric dispersion curves (C. Prodan and E. Prodan, Dielectric behavior of living cell suspensions, *J. Physics D: Applied Physics* 32 (1999), no. 3, 335-343). When an external electric field is applied, the charges surrounding the membrane move, creating an electric dipole. In the alpha dispersion region, the dipole is very large, leading to an extremely high dielectric permittivity. To give an example, the dielectric permittivity of a suspension of live cells can be $10^6$ times larger than that of the vacuum (R. D. Stoy, K. R. Foster and H. P. Schwan, Dielectric properties of mammalian tissues from 0.1 to 100 MHz: A summary of recent data, *Phys. Me. Biol.* 27 (1982), no. 4, 501; C. Prodan, F. Mayo, J. R. Claycomb, J. H. Miller Jr and M. J. Benedik, Low-frequency, low-field dielectric spectroscopy of living cell suspensions, *J. Applied Physics* 95 (2004), no. 7, 3754-3756).

Due to relatively small mobility, the charges cannot follow the electric field at higher frequencies. This region can range from 1 Hz to 1 MHz. The dielectric curve drops at some point into another regime, called the beta plateau. The dielectric permittivity is still much larger than that of the substances found in the cell or medium and its value is typically in the hundreds. The existence of the beta plateau is due to the presence of the membrane. At even higher frequencies, typically above $10^5$ Hz, the dispersion curve drops again into another regime, called the gamma plateau. At these frequencies, the molecular structures become important and the value of the dielectric permittivity becomes comparable to that of the substances found in the solution. The frequency range most relevant to the present invention is 1 Hz to 32 MHz. In this range, the electromagnetic field cannot be used to distinguish the very fine structure of the cell but provides an effective image of the cell. In a preferred embodiment, the frequency range is from 1 Hz to 10 kHz.

The theory of the dielectric behavior of live cells suspensions as described herein was built on a minimal set of assumptions and requires, at the input, a set of parameters that are directly measurable, such as the cell's membrane thickness, dielectric composition, cell concentration. It takes into account the diffusion of charges along the membrane's surfaces. The model can be effectively and accurately applied to any cell shape and distribution in cell orientation, in particular, a random orientation of the suspended non-spherical cells. At a qualitative level, the theory correctly accounts for the dielectric behavior of live cells over the entire range of α and β regimes.

It is assumed that the dielectric response of live cell suspensions, in alpha and beta range of frequencies, is the same as that of a suspension of shelled dielectric particles, with a negative (positive) superficial distribution of charges, bound to the inside (outside) face of the shell. These charges can move on the faces of the shell but they cannot leave the shell's surfaces. The complex dielectric constant of a suspension of such particles was computed using the Lorenz formula, $$\varepsilon_{sus}(\omega) = \varepsilon_0^*\left(1 + \frac{p\alpha(\omega)}{1 - p\alpha(\omega)/3}\right),$$

$$\text{with } \vec{\alpha}(\omega) = \frac{1}{VE_0}\int_V dV \frac{\varepsilon^* - \varepsilon_0^*}{\varepsilon_0^*}\langle\vec{E}(\omega)\rangle,$$

where $\in_0^*$ is the complex dielectric function of the medium, p is the volume concentration of the solution and $\alpha(\omega)$ is the magnitude of the frequency dependent polarizability (D. J. Bergman, Bounds for the complex dielectric constant of a two-component composite material, *Physical Review B* 23 (1981), 3085-3065). The integral above is over the particle's volume V, E is the non-uniform complex dielectric function of the composite particle and $\alpha(\omega)$ is the electric field inside the particle when the particle is placed in a homogenous, time oscillating electric field of amplitude $\overline{E}_0$ and pulsation $\omega$. The brackets indicate the average of $\overline{E}(\omega)$ over particles orientations.

$\overline{E}(\omega)$ can be computed by solving the Laplace equation for the electrical potential, $\Delta\phi=0[\phi(\overline{r})\to\overline{r}E_0$ for $r\to\infty]$ together with the boundary conditions at the interfaces, where the bound superficial charge distribution $\rho$ leaves: $\overline{n}(\sigma^+\overline{E}^++\partial_t\overline{D}^+)-\overline{n}(\sigma^-\overline{E}^-+\partial_t\overline{D}^-)=\partial_t\rho$. Here, +/− indicates the outside/inside face of the interface, $\overline{n}$ is the normal to the interface and $\overline{E}$ and $\overline{D}$ are the electric and induction fields, respectively. These boundary conditions are applied on both faces of the membrane. If $\overline{j}_\Sigma$ is the electrical current of these charges, then the continuity equation $\vec{\nabla}\vec{j}_\Sigma+a\partial_t\rho=0,b$ should be considered, where $\nabla_\Sigma$ is the gradient operator of the interface. The system of equation is mathematically closed once one gives an expression for $\overline{j}_\Sigma$ which is made up of a conduction part and a diffusion part: $\overline{j}_\Sigma=-\gamma\nabla_\Sigma\phi-D\nabla_\Sigma\rho$, where $\gamma$ is the conductivity and D is the diffusion constant of the bound charges.

The membrane potential enters in this picture in an indirect way. The conductivity $\gamma$ of the bound charges is given by $\gamma=u\rho$, where u is the mobility constant. In the limit of small external fields, one can assume that $\gamma$ is fixed by the equilibrium charge distribution $\rho_0$. It turns out that, in the absence of any external field, the system of equations can be solved exactly even for arbitrary geometries, leading to a constant, positive (negative) distribution $\rho_0$ $(-\rho_0)$ of the bound charges on the outer (inner) face of the shell and to a constant electrical potential difference $\Delta V_0$ between the shell's faces. The value of $\Delta V_0$ is determined by how much negative charge Q is trapped inside the membrane. Q is an independent parameter that needs to be supplied from experiment or by other means. Equivalently, one can identify $\Delta V_0$ with the resting membrane potential and let $\Delta V_0$ be an input parameter for the microscopic theory. The conclusion, so far, is that the membrane potential fixes the conductance of the bound charges: $\gamma=\pm uc\Delta V_0$, where c is the membrane's capacitance per unit surface area. The diffusion constant D is also proportional to the mobility u, which means the ratio $\gamma/D$ is directly proportional to the membrane potential and independent of the mobility u.

In the non-equilibrium case, the system of equations was reduced to an integral equation by using a single layer expression for the electrical potential (D. Vranceanu and E. Gheorghiu, Shape effects on the dielectric behavior of arbitrarily shaped particles with particular reference to biological cells, *Bioelectrochemistry* 40 (1996), 167-170.), equation that was solved using spectral methods. The operator:

$$\hat{E}[\mu](\overline{x}) = \frac{1}{4\pi}\int_S \frac{(\overline{x}-\overline{y})\cdot\overline{n}_x}{|\overline{x}-\overline{y}|^3}\mu(\overline{y})dS_y$$

($\overline{n}_x$ being the normal to the surface at $\overline{X}$) is used, acting on the square integrable functions $\mu$, defined on the outer cell's surface S. Using its spectral decomposition, $\hat{E}=E_n\chi_n\hat{P}_n[\chi_n$ are the eigenvalues and $\hat{P}_n$ are the corresponding spectral projectors], the following compact, explicit formula is obtained:

$$\alpha(\omega) = \frac{1}{3V}\sum_{n,i}\left[\begin{array}{c}\frac{\lambda_n}{1/2-\chi_n\lambda_n}\langle\overline{x}\cdot\overline{e}_i|\hat{P}_n|\overline{n}\cdot\overline{e}_i\rangle - \\ \frac{(1/2-\chi_n)(\tilde{\varepsilon}_n^*-\varepsilon_0^*)}{\tilde{\varepsilon}_n^*}\langle\overline{x}\cdot\overline{e}_i|\hat{P}_n|\mu_\alpha^i\rangle\end{array}\right],$$

where $\lambda_n = \frac{\tilde{\varepsilon}_n^* - \varepsilon_0^*}{\tilde{\varepsilon}_n^* + \varepsilon_0^*},$ $$\tilde{\varepsilon}_n^* = \varepsilon_1^*\frac{\chi_n + 1/2 + \delta[(\varepsilon_2^*-\varepsilon_1^*)/2(\varepsilon_2^*+\varepsilon_1^*)-\chi_n]}{\chi_n - 1/2 + \delta[(\varepsilon_2^*-\varepsilon_1^*)/2(\varepsilon_2^*+\varepsilon_1^*)-\chi_n]},$$

with $\delta$ being the ratio between the volumes enclosed by the outer and inner surfaces of the membrane. (See M. Stipanuk, *Biochemical and physiological aspects of human nutrition*, W. B. Saunder Company, Philadelphia, 2000). Also, $\overline{e}_1$ (i=1, 2, 3) denote three orthonormal vectors and $\mu_\alpha^i$ is the single layer distribution of charges that sets in when $\overline{E}_0$ is along direction $\dot{e}_i$. The above expression can be evaluated for arbitrarily shaped particles. The first term in the above expression for $\alpha(\omega)$ describes the $\beta$-effect, while the second term describes the $\alpha$-effect. For spherically shaped particles, it takes the following form:

$$\alpha(\omega) = \frac{6\lambda_1}{3-\lambda_1}\left[1 - \frac{2R\gamma/D}{\left(1+j\omega\frac{R^2}{2D}\right)(3-\lambda_1)(\tilde{\varepsilon}_1^*+\varepsilon_0^*)+2R\gamma/D}\right],$$

where $\lambda_1$ and $\tilde{\in}_1^*$ are computed as above using $\chi_1=\frac{1}{6}$.

To evaluate the above microscopically derived formulas, one needs 7 cell parameters: the thickness d, radius R and dielectric permittivity $\in_1$ of the membrane, the dielectric permittivity and conductivity ($\in_2$, $\sigma_2$) of the core of the cell, the mobility u of the superficial charges and the membrane potential $\Delta V_0$. It is more convenient to use the conductivity $\gamma$ and diffusion constant D of the bound charges as input parameters. In this case, the value of u is set by D and the value of $\Delta V_0$ by the ratio $\gamma/D$. The volume concentration p of the suspension, the shape of the cells and the dielectric permittivity and conductivity ($\in_0$, $\sigma_0$) of the host medium are also specified. All these parameters are directly obtainable from either the literature, which provides many of the parameters for known cells. Alternatively, these parameters can be obtained experimentally by methods known in the art.

In one embodiment, transmitted light microscopy is employed to measure the size and shape of the cells to be used. The cells are imaged in an inverted microscope and the image is recorded on a computer. The size and shape of a large number of cells is extracted from the images and a statistical analysis is performed to determine a unique, effective size and shape of the cells.

The exact value of the membrane thickness, can be anywhere between few nanometers and hundreds of nanometers. The thickness of lipid bilayers, as reported in many studies, is in between 2 nm and 10 nm and sometime larger. Since the dielectric response of live cell suspensions is extremely sensitive to this parameter, it is carefully measured in this embodiment of the invention. In one embodiment of the invention, the thickness of the membrane of the cells used in the experiments is measured. The cell is embedded in a resin medium, sliced in thin layers using a microtone and then stained, all of these following existing established protocols (M. David, M. Gabriel and M. Kopecka, Unusual ultrastructural characteristics of the yeast malassezia pachydermatis, *Scripta Medica Facultatis Medicae Universitatis Brunensis Masarykianae* 76 (2003), no. 3, 173-186; 49. D. J. Silverman and C. L. Wisseman Jr, Comparative ultrastructural study on the cell envelopes of *rickettsia prowazekii, rickettsia rickettsii*, and *rickettsia tsutsugamushi, Infection and Immunity* 21 (1978), no. 3, 1020-1023; and S. P. Schenk and O. Wyss, Influence of oxygen on phospholipid production and colony formation in a nitrogen fixing mutant of *azotobacter vinelandii, J. Bacteriology* 130 (1977), no. 3, 1382-1386). The sample is imaged using an electron microscope and the thickness of the membrane is extracted from the images.

Removal of the Polarization Effect

The polarization effect is a classic source of error when measuring the dielectric dispersion curves, especially at low frequency. This error can be removed through calculating the polarization effect and subtracting it from the signal. Techniques such as the distance variation technique can be used to remove this error (C. Prodan, et al., *J. Applied Physics* 95 (2004), no. 7, 3754-3756). However, this technique works well only for low salt concentration in the solution to be measured. Thus, for accurate calculations, the cell solutions used in the present inventions should be suspended in water or a low ionic strength buffer for the measurement (i.e., after they are grown in buffer to saturation point).

Alternatively, the polarization effect can be reduced by coating the electrodes with different films, such as platinum, platinum black or polymers. The coating material should expand the present limitations of the distance variation technique, and allow for accurate dielectric measurements at higher salt concentrations. The preferred coating materials may be obtained by coating an electrode and testing the coating film by measuring the dielectric permittivity of salty water. The salt should not affect the dielectric permittivity of the solution, which should remain flat at $\epsilon=78$. The salt concentration can be systematically varied and the experimental output is compared to this value. Thus, the preferred coating material is obtained.

Although the exemplified experimental setup (see FIG. 1) is capable of highly accurate impedance measurements at low frequencies, the measured impedance doesn't necessarily reflect the true impedance of the solution. In general, the impedance of the probe is contaminated by the so called "polarization" impedance, $Z_P$, which occurs at the interface between the fluid and metallic electrodes.

Figure 2:
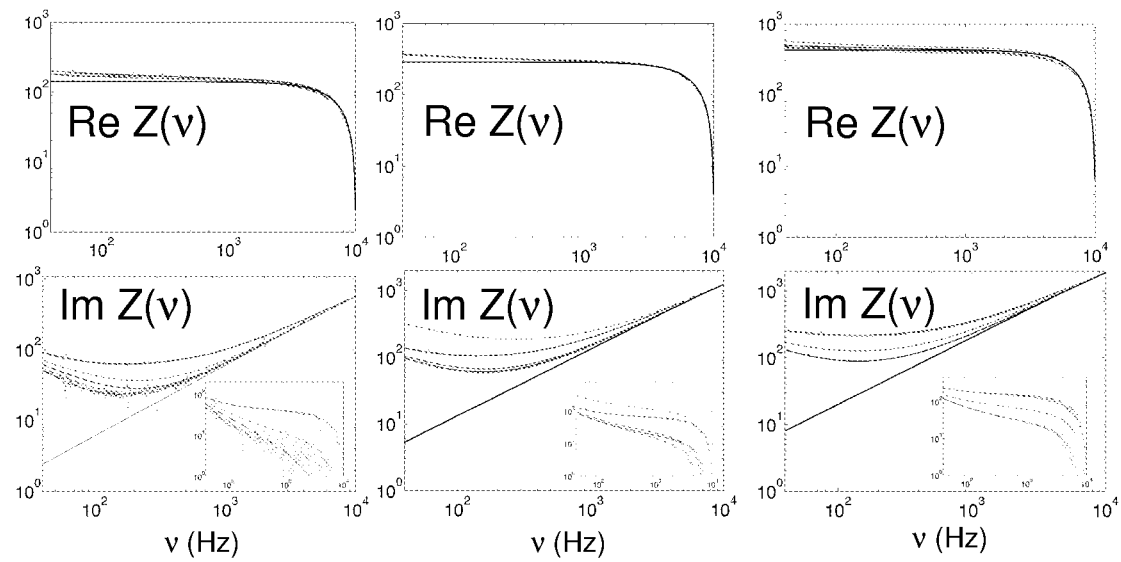
FIG. 2. Real (first row) and imaginary (second row) parts of the probe impedance for d=1 mm (first column), d=3 mm (second column) and d=5 mm (third column), for 0.01, 0.03, 0.05, 0.07, and 0.09 applied V/mm, where the highest impedance for d=1 mm is at 0.01 M/mm, the highest impedance for d=3 mm is 0.09 V/mm, and the highest impedance for d=5 mm is 0.01, 0.07, and 0.09 V/mm.

FIG. 2 shows how one can measure $Z_P$ and, more importantly, how one can map its dependency on all these tree parameters. For example, purified water was used for the frequency dependent impedance of the probe for three values of d. For each d, the experiments were repeated with five values of the applied voltage per centimeter. The 30 curves were then fitted with an ideal impedance, $Z_{ideal}=d/j\omega\epsilon^*S$, with a higher weight at larger frequencies, where the polarization effects are expected to be negligible. Following this procedure, it was found that $\epsilon^*=\epsilon+1/j\omega\sigma$, with $\epsilon=77$ and $\sigma=0.00016$. Once these values were determined, $Z_{ideal}=d/j\omega\epsilon^*S$, was plotted for each distance. The difference between the measured impedances and $Z_{ideal}$ is precisely the polarization impedance $Z_P$, which is shown in the insets.

This same experiment can be performed with a buffer, where, since the solution is ionic, the polarization effect extends to higher frequencies. Thus, the polarization impedance $Z_P$ can be removed from the measured impedance.

$Z_P$ is mainly reactive, as previously predicted (Schwan, 1966; 1968). In the log-log plot of the insets in FIG. 2, the curves appear linear for a wide range of frequencies, implying that $Z_P$ goes as a power law with the frequency (McAdams, 1994). The power law can be easily computed from the graphs. This specific behavior was used in the past to successfully remove the polarization impedance (Bordi, 2001). Both the constant in front and the exponent of the power law appear to be weakly dependent on the applied voltage.

Figure 5:
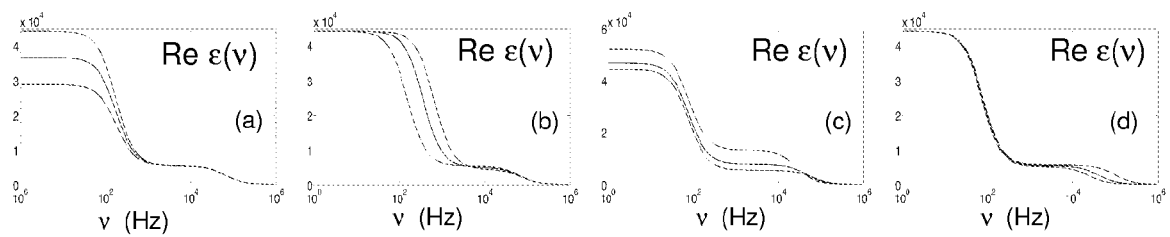
FIGS. 5(a)-5(d). Theoretical dispersion curves for different: (a) membrane potentials: γ/D=0.1 (top), 0.08 (middle) and 0.06 (bottom), (b) charge mobility: $D=10^{-7}$ (bottom), $5 \times 10^{-7}$ (middle) and $10^{-8}$ (top), (c) membrane thickness: $d=7 \times 10^{-9}$ (bottom), $5 \times 10^{-9}$ (middle) and $3 \times 10^{-9}$ (top), (d) conductivity of the medium: $\sigma_0 = 0.005$ (bottom), 0.01 (middle) and 0.05 (top). If not specified, the parameters were given the following values: $R=20 \times 10^{-6}$, $d=7 \times 10^{-9}$, γ/D=0.1, $D=10^{-7}$, $\varepsilon_0=80$, $\varepsilon_1=4$, $\varepsilon_2=80$, $\sigma_0=0.005$, $\sigma_1=0$, $\sigma_2=0.1$, p=0.3. The units are in S.I and the shape of the cells was assumed spherical.

$Z_P$ also saturates at large values of d, fact that justifies the use of "electrode distance variation technique" to correct for the polarization effect [x]. This technique works as follows: one measures the impedance for two different electrode positions $d_1$ and $d_2$, well in the saturation region, where the following general equations apply: $Z_s^1+Z_p=Z^1$, $Z_s^2+Z_p=Z^2$, L where $Z_s^{1,2}$ are the impedances of the sample for the two electrode positions. By subtraction, $Z_s^1-Z_s^2=Z^1-Z^2$, L a result that is independent of polarization impedance. For parallel electrode plates, the equation becomes $$Z^1 - Z^2 = \frac{d_1 - d_2}{(\sigma + i\omega\varepsilon)S},$$

which provides a simple way of extracting the permittivity and conductivity. FIG. 5 shows an example of polarization removal for the pure water. The experiments were conducted with gold plated electrodes, which are known to induce large polarization effects, which can be seen in the un-processed curves. Still, within the range from 100 Hz to 10 kHz, the technique gives a value that is accurate to within less than 5%.

Cells

A variety of mammalian cells can be assayed using the methods of the present invention. The cells may be primary or cell lines that are transfected either stably or transiently to express an ion channel.

The cell lines that are particularly preferred for screening of human therapeutics include tissue culture cell lines that can be relatively easily grown, and can be readily transfected with high efficiency such as those available through the American type culture collection (ATCC) see (http://www.atcc.org), and the European collection of cell cultures (ECACC) (http://www.camr.org.uk).

Additionally in some cases primary cell lines, or tissue slices may also be preferred for screening when it is required to express, or measure, the response of the ion channel of interest in its native physiological context. This approach is particularly useful for screening for specificity, selectivity or toxicity of candidate therapeutics.

For assays performed on cultured cell lines, one selection criteria is the resting transmembrane potential of the cell line, and the presence of endogenously expressed ion channels. The selection of appropriate cell lines for specific ion channels of interest is dependent on the voltage dependent properties and ion selectivity of the ion channel of interest.

In some cases it is desirable to use a cell line which has no (or very low) detectable endogenous expression of other ion channels. Cells of this type can be exemplified by HEK-293, COS-7, CHO-K1, CHL, and LTK(−) cells. These cells inherently have a resting potential in the range of +10 to −30 mV, which is above the activation and inactivation thresholds of most voltage-dependent channels. Use of these cell lines has the advantage that the ion channel of interest is the major modulator of transmembrane potential within the cells so that screening assay data are generally easily and unambiguously interpreted.

In one embodiment, it may be necessary to maintain a voltage-regulated ion channel at a highly polarized transmembrane potential. For example, for some cells, in order to assay an ion channel in the resting state, the membrane potential must be maintained below the threshold activation potential of the ion channel. In this case, the transmembrane potential can be controlled via the expression of a second ion channel. For example, two ion channels are co-expressed such that one channel can maintain the resting transmembrane potential of the cell at a particular voltage (i.e., −90 mV) or identify a cell line that endogenously expresses similar ion channel. In other cases it may be necessary to use the expression of a second ion channel, in conjunction with electrical stimulation to drive the cell membrane to a specific transmembrane potential, to enable the first ion channel of interest to be assayed.

The cells are measured in a physiological buffer and could be either in suspension or adherent. Since the shape of the cells may change when adherent on a surface, the shape calculation will be modified to account for the polarizability of the different shapes.

Transfection of Ion Channels

Nucleic acids used to transfect cells with sequences coding for expression of the ion channel of interest are typically in the form of an expression vector including expression control sequences operatively linked to a nucleotide sequence coding for expression of the channel. The nucleotide sequence coding for expression of a channel is a sequence that, upon transcription and translation of mRNA, produces the channel. This can include sequences containing, e.g., introns. The expression control sequences are nucleic acid sequences that regulate the expression of a nucleic acid sequence to which it is operatively linked Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, and maintenance of the correct reading frame of that gene to permit proper translation of the mRNA, and stop codons.

Methods which are well known to those skilled in the art can be used to construct expression vectors containing the ion channel coding sequence, operatively coupled to appropriate localization or targeting domains and appropriate transcriptional/translational control signals. These methods include in vitro recombinant DNA techniques, synthetic techniques and in vivo recombination/genetic recombination. (See, for example, the techniques described Sambrook et al. (2001) *Molecular Cloning: A Laboratory Manual.* 3rd ed. Cold Spring Harbor Laboratory Press: Cold Spring Harbor, N.Y. Many commercially available expression vectors are available from a variety of sources including Clontech (Palo Alto, Calif.), Stratagene (San Diego, Calif.) and Invitrogen (San Diego, Calif.) as well as and many other commercial sources.

A method of transfecting cells is to use inducible controlling nucleotide sequences to produce a sudden increase in the expression of the ion channel of interest e.g., by inducing expression of the channel. Example inducible systems include the tetracycline inducible system first described by Bujard and colleagues (Gossen and Bujard (1992) *Proc. Natl. Acad. Sci. USA* 89 5547-5551, Gossen et al. (1995) *Science* 268 1766-1769) and described in U.S. Pat. No. 5,464,758.

Method of transfecting cells include transfection of DNA as calcium phosphate co-precipitates, conventional mechanical procedures such as microinjection, electroporation, insertion of a plasmid encased in liposomes, or virus vectors may be used. Eukaryotic cells can also be co-transfected with DNA sequences encoding the ion channel, and a second foreign DNA molecule encoding a selectable phenotype, such as the herpes simplex thymidine kinase gene. Another method is to use a viral vector, such as simian virus 40 (SV40) or bovine papilloma virus, to transiently infect or transform eukaryotic cells and express the ion channel. (Eukaryotic Viral Vectors, Cold Spring Harbor Laboratory, Gluzman ed., 1982).

Selection of stable clones will typically be made on the basis of successful expression of the ion channel of interest at sufficient level to enable its facile detection. In many cases this analysis will require functional characterization of individual clones to identify those that exhibit appropriate electrophysiological characteristics consistent with expression of the clone of interest. This analysis can be completed via the use of patch clamping, or via the measurement of transmembrane potentials using transmembrane potential sensitive dyes as described below. An advantage to the use of this latter method is that it is compatible with fluorescence activated cell sorting and provides for the rapid analysis of many thousands of individual clones per second. In some cases where the sodium channel is electrically silent in the resting cell, confirmation of expression can also be readily achieved by immunochemistry using antibodies raised against the native ion channel, or a defined epitope introduced in the ion channel via molecular techniques as described above.

In cases where cells are transfected with a first ion channel of interest, and a second ion channel to set the transmembrane potential, it is preferable to optimize the relative expression of both ion channels. Typically the optimal relative expression of the two ion channels is determined empirically by selecting clones that provide the maximum dynamic range and minimal statistical variation in their response.

Ion Channels

Ion channels are pore-forming proteins that allow the passive diffusion of ions across the cell membrane. The ionic species ($Na^+$, $K^+ Ca^{2+}$, and $Cl^-$) are moved between cellular compartments.

Ion channel dysfunction has been implicated in diseases and disorders such as Parkinson, epilepsy, Bartter's syndrome, cystic fibrosis, diabetes, erectile dysfunction, epilepsy (up-regulation in epileptic hippocampus tissue (Whitaker et al. (2001)), heart failure, hypertension, muscular sclerosis, obesity, schizophrenia, schizo-affective disorder and sickle cell anemia. Other diseases and disorders associated with ion channel disfunction are neuropathic pain, chronic pain, anxiety, seizure, ischemia, migraine, bipolar disorder, deafness, Alzheimer's disease, stroke, Parkinson's disease, tinnitus, depression and substance abuse, asthma and chronic stress. Additionally, prostate cancer and other cancerous tissues express high levels of ion channel (prostate cancer tissues expresses the sodium ion channels Nav1.3 and Nav1.7). Over 6 billion dollars in yearly sales and 15% of the top selling drugs are targeted for ion channels. In addition, over 500 human ion channel genes have been identified, yet only around 40 have been targeted for therapeutic effects.

Voltage-dependent potassium channels repolarize nerve and muscle cells after action potential depolarization. They also play important regulatory roles in neural, muscular, secretory, and excretory systems. Most cells actively maintain a high intracellular potassium concentration, so that the reversal transmembrane potential for potassium is around −90 mV. Potassium typically flows out of the cell, so that opening more potassium-selective channels tends to drive the transmembrane potential more negative, in contrast to sodium channel opening that typically drives the transmembrane potential more positive.

A listing of various potassium ion channels is provided in U.S. Pat. No. 6,686,193, herein incorporated by reference. These ion channels include channels which are ATP regulated (rKir), constitutively active (Kir2), G-protein regulated (Kir3), voltage regulated, Kv2, Kv3, Kv4, delayed rectifier, $Ca^{2+}$ regulated big, medium, and small (KCNN), rectiviers (KA), intermediate conductance channel (IKCa), arachidonic acid/fatty acid modulated K+ channel (KA4), Acetylcholine-activated K+ channel (KACh), inward rectifiers (KIR), and transient outward.

The family of sodium channels has nine known members, with amino acid identity >50% in the transmembrane and extracellular loop regions. The proteins of these channels are named Nav1.1 through Nav1.9.

Potassium channels show enormous diversity in terms of activation and inactivation time constants and voltage dependencies. In general, voltage-dependent potassium channels show voltage dependence similar to sodium channels, being closed at very negative potentials and opening above a certain threshold. Potassium channels may have multiple resting states, multiple inactivated states, and typically a single activated state. Unlike voltage-dependent sodium channels, transitions are allowed between most states, including activation, deactivation, inactivation, release from inactivation, and flickering.

In one aspect of the present invention, more than one ion channel will be used in an experiment to determine if the test compound(s) are modulators of any of the selected ion channels. In one embodiment, cells containing multiple ion channels will be assayed with the test agents. For any test agent modulating the membrane potential in the combined experiment, each ion channel will be expressed individually and the test compounds re-run to determine which ion channel was modulated. In another embodiment, the test compounds will be exposed to a number of different ion channels where different chambers (or the same chamber in a sequential analysis) are used for each of the cells expressing each ion channel.

hERG

The hERG (human ether-a-go-go related gene) potassium channel is required for normal cardiac repolarization, is susceptible to inhibition by a wide variety of compounds, and its blockage can lead to cardiac QT interval prolongation and life threatening arrhythmias such as Torsades de Pointes. Thus, early screening of compounds for hERG channel activity is particularly useful in the drug-discovery process.

hERG-expressing cells are mammalian cells, large in size (up to ~30 μm in diameter) and spherical in shape when suspended in the buffer solution. They can be replated twice a week and are grown on a flat surface (flasks). An enzyme, trypsin, can be used to remove the cell from the surface, followed by a gentle resuspension in solution. The membrane potential of the HEK-293 cells can be modulated by using different concentrations of $K^+$ outside or by the use of a potassium ion channel blocker such as quinidine.

Because of the spherical shape of the cells, the theoretical calculations based on a spherical shape having a core and shell (i.e., membrane) layer is appropriate.

Combinations

While the present invention provides a novel means of determining membrane potential, the dielectric spectroscopic method can simultaneously be used to determine additional information about the cell. Fore example, information on cell size, membrane capacitance, and cytoplasm conductivity as a function of frequency can be obtained from the DS data (see Cheung K, Cytometry A. 2005 June; 65(2):124-32). The concentration of the cells in the solution can be calculated using DS as well. The theory of cell's dielectric response can be used to obtain the changes in the ionic concentrations in and outside the cells during the experiments. This information is used to characterize the ion transfer through the membrane during these processes.

In addition, other techniques for characterizing either the cell or the active agent at the same time as the DS measurement is being obtained or processesed may be used.

Modulators of Ion Channels

Ion channels may be activated, deactivated, inactivated, or released from inactivition, or flicker. This can be accomplished by adding a modulator of the ion channel into the chamber. The modulator may be an antagonist or agonist of the ion channel The modulator may modulate potassium, sodium, calcium, or a chloride ion channel.

Usually a small quantity (μM) of blockers is enough to induce large changes in the membrane potential. Since the blockers embed themselves in the membrane, they don't change the conductivity of the solution, thus don't change the polarization effect. The shape and size of the cells remain unchanged with the addition of ion channel modulators.

Ion channel modulators include antiarrhythmic agents and antihistamines. Antiarrhythmic agents can be divided into 4 classes, depending on the mechanism of action. These classes include a) quinidine: class 1 agent, and b) propranolol: class 2 agent (also known as beta blockers), c) sotanol: class 3 agents and d) verapamil or diliazem: class 4 agents (also known as $Ca^+$ channel blockers). Antihistamine agents having cardiotoxicity side effects include astemizole and terfenadine. Both of these drugs were sold on the market then withdrawn due to long-term effects on the heart. These ion channel modulators may be analyzed as test agents. Further, compounds and compound libraries having similar proposed mechanisms of action may be screened using the methods as described herein.

Measuring Membrane Potential

The analytical and experimental techniques discussed herein are combined to create a fast, non-invasive tool for measuring and monitoring the membrane potential and other cell parameters. The DS and theoretical modeling can be incorporated into an integrated platform that will take the experimental dispersion curves and fit them with the theoretical model.

DS measurements for the mammalian cell are obtained in the alpha dispersion range. The alpha dispersion is proportional to the membrane potential whereas the beta dispersion is not. Thus, the present invention uses the frequency range associated with the alpha dispersion. It is possible to account for the non-linearity of the beta dispersion and thus use a frequency range of between 1 and 32 MHz. In one preferred embodiment, the membrane potential is obtained from 1 Hz to 10 KHz, i.e., within the alpha dispersion range. In another preferred embodiment, the measurement is obtained between 100 Hz and 10 kHz. In yet another preferred embodiment, the measurement is obtained between 100 Hz and 1 kHz.

Then, experimentally measured or literature-based values are assigned to all the cell parameters, except the membrane potential, which is left as a fitting parameter.

Variations in the membrane potential are induced by adding an ion channel modulator and the whole procedure is repeated.

Variations in different cell parameters can have strong and independent effects on the dielectric dispersion curves. This means that one can simultaneously extract, with high accuracy, more than one cell parameter.

The dielectric spectroscopic method of the present invention, without any post-data processing is modeled in FIGS. 4(a) and (a'). These figures demonstrate what occurs when the probe was replaced with a parallel RC circuit of nominal values of R=1000Ω and C=0.1 μF (with 10% accuracy). The graphs demonstrate that both measured values are within 1% of the nominal values even at the very low frequency range. FIG. 4(b) illustrates the value of the relative permittivity of air as extracted from the measured impedance Z with the probe kept in the air, via $Im(1/Z)=\omega \in S/d$, with S the active surface of the electrodes and d the distance between them. The value of permittivity is remarkably closed to 1, given that no calibration was used in this experiment. The post-processing described in the next paragraphs renders the measured permittivity exactly to 1.

FIG. 5 shows examples of theoretical dispersion curves for dielectric permittivity. In all these examples, there is a high resemblance between the theoretical curves and the ones observed experimentally in both alpha and beta ranges of frequencies (F. Bordi, C. Cametti and T. Gili, Reduction of the contribution of electrode polarization effects in the radio wave dielectric measurements of highly conductive biological cell suspensions, *Bioelectrochemistry* 54 (2001), 53-61.). Panels shows the strong dependence of (a) the α-plateau on the membrane potential, (b) the length of the α-plateau on the mobility, (c) the α-plateau on membrane thickness (the α-plateau is also rigidly raised) and (d) the length of the α-plateau on the conductivity of the medium.

In one embodiment, the membrane potential of the mammalian cells is first be measured using voltage sensitive dyes or patch clamp. By comparing the results the voltage sensitive dyes and patch clamping, any problem of membrane potential homogeneity in suspension measurements can be addressed before dielectric spectroscopy measurements are obtained. This will provide the membrane potential distribution within a suspension, which can be address in the dielectric measurements. Preferably, these measurements are performed for various concentrations of cells.

Preferably, the optimal concentration limits for the dielectric method is established for the mammalian cell line. Different concentration of cells may be measured. The smallest concentration will provide the lowest limit at which the membrane potential can be determined, while the larger concentration will provide information about the upper concentration limit in which the model is applicable. Part of this data includes the variation of the applied electric field (from 0.1 V/cm to 1V/cm) that can be important at low cell concentration.

Arrays and High-Throughput Screening

The method of the present invention may be used to determine the membrane potential of a singe cell sample. However, is useful as a means for high-throughput screening arrays as well as other forms of multi-sample analysis. The present method is non-evasive, fast, and cost effective. It also does not require a highly skilled operator to run. Thus, the present invention is preferably used for high-throughput screening assays.

Experiments using beaker-sized chambers provide the average change in the membrane potential of the solution. However, as the chamber size is reduced and the cell concentration is lowered, the impedance measurement will start to resemble single cell measurements. Both DS and the theoretical model provided herein are applicable for analysis of single cells.

In an aspect of the present invention, a device as is commonly used by fluorescence activated cell sorting (FACS) is used. The FACS flow cytometry apparatuses relays upon the flow of cells or other particles in a liquid flow stream. A liquid sample containing cells is directed through the flow cytometry apparatus in a rapidly moving liquid stream so that each cell passes serially, and substantially one at a time, through the chamber. Cell volume may be determined by changes in electrical impedance as each cell passes through the sensing region. Independently, an incident beam of light may obtain additional information about the cell. Cell sorting may also be achieved using such a device. FACS instruments are known in the art, and are described, for example, in U.S. Pat. No. 4,348,107 and in Practical Flow Cytometry 4$^{th}$ edition, by Howard M. Shapiro, and in *Flow Cytometry First Principles*, 2$^{nd}$ edition by Alice Longobardi Givan In one aspect of the present invention, multiplex screening of test agents is performed with a microcolumn flow cell which is automated using multiple fluid injection ports and two or more electrodes within the flow cell tubing or chamber of the device. Such devises are described, for example, by Bruckner-Lea C J et al., *Anal Chem.* 2000 Sep. 1; 72(17): 4135-41.

In another embodiment a typical 96-well multiwell plate having electrodes within each well is used to provide a multiplex analysis of the membrane potential of multiple test agents.

In another embodiment, the method of the present invention analyzes cells using microfluidic chips for highly miniaturized electrical stimulation and analysis. Such systems include those, for example, described in U.S. Pat. No. 5,800,690 to Chow et al., European patent application EP 0 810 438 by Pelc et al. and PCT application WO 98/00231 by Parce et al. These systems typically use electrogenic fluid movement to manipulate small fluid volumes within microcapillaries present on glass or silicon chips. In one particular embodiment, the microfabricated fluorescence-activated cell sorter described by Fu et al. (*Nature Biotechnology* 17:1109-11, 1999) could be easily modified to have a pair of electrodes placed in, or near the optical interrogation region.

In a preferred multiplex system, the system allows for addition of the cells to the chamber, addition of the test agent to the chamber, washing the chamber to remove the test agent, and then addition of a second test agent (or second concentration of the same agent) to the chamber.

In another embodiment, each cell or cell and test agent will only be measured once. The theoretical calculations are then performed on the average of multiple DS measurements.

EXAMPLES

The present invention is further illustrated in the following examples, which should not be taken to limit the scope of the invention.

Example 1 hERG cells used in the experiments are treated following the standard protocol: incubated at 37 degrees at 5% $CO_2$ in DMEM media (with 10% fetal calf serum, penicillin streptomycin and 2 mM L-glutamine). When 80% confluent they are split and re-incubated. When the cells are needed for the experiment the flasks is treated with trypsin, incubated for 10 minutes. Trypsin is an enzyme that removes the cells from the flasks by cleaving. The cells are then gently diluted into DMEM media with 20% fetal calf serum (to annihilate the effects of trypsin) then span at 1000 g for 8 minutes. The pellet is gently and slowly resuspended in Tyrode's buffer for dielectric measurements.

Example 2

The solution to be measured is placed in a small, 30 ml glass beaker with 2 gold-plated flat circular plate electrodes as shown in FIG. 1. A Signal Analyzer SR80A provides a sinusoidal voltage at its signal output. It also digitizes the voltage at Channels 1 and 2 and takes the ratio of these two as function of frequency. The real and imaginary of this ratio is stored on a computer. The bottom electrode plate is held at ground potential through the negative input of the Amplifier A2. The output voltage from the Signal Analyzer is applied to the upper electrode, through resistor R1. As a result, the current I that flows through the cell suspension produces a voltage $V_1$, equal to the product of I and impedance Z of the probe. The voltage $V_2$ is equal to minus the product of I and resistance R2. Thus the transfer function, T, is directly related to the cell suspension impedance by: $T = V_1/V_2 = Z/R_2$. The complex dielectric function is then extracted from Z. All the electronic components are finely tuned to minimize the noise in the low frequency regime.

Example 3

Activity of hERG Ion Channels in the Presence of Antiarrhythmic Agents and Antihistamines with Carditoxicity Effects The hERG ion channel activity is studied on HEK-293 cell line with overexpresses hERG ion channels. Antiarrhythmic agents tested include quinidine, a class 1 agent, and propranolol, a class 2 agent. An antihistamine agent, astemizole, was also tested. For these compounds, the membrane potential variation was determined by dielectric spectroscopy and the $IC_{50}$ curve is compiled. The results from the dielectric spectroscopy are then closely compared with patch clamping experiments done in parallel. The compounds analyzed herein were chosen to test a large range of potency. For example, 2 μLM quinidine is needed to block 50% of the hERG channels while only 1.3 nM astemizole is required to produce the same effect.

HEK-293 cells: Determining Drug Potency Using DS. Comparison with Traditional Methods The cells used in the experiments were treated following the standard protocol: incubated at 37° C. at 5% $CO_2$ in DMEM media (with 10% fetal calf serum, penicillin streptomycin and 2 mM L-glutamine). When 80% confluence was reached, they were split and re-incubated. When the cells were needed for the experiment the flasks were treated with trypsin and incubated for 10 minutes. Trypsin is an enzyme that removes the cells from the flasks by cleaving. The cells were then gently diluted into DMEM media with 20% fetal calf serum (to annihilate the effects of trypsin) then spun at 1000 g for 8 minutes. The pellet was gently and slowly resuspended in Tyrode's buffer to an OD=0.05 for dielectric measurements and patch clamp measurements.

Analyses of three different drugs, ion channel blockers, which have different action mechanism are presented. Two of the drugs, quinidine and propranolol are antiarrhythmic drugs while the third, astemizole, is an antihistamine. To assess the potency of pharmacological agent, the $IC_{50}$ curves were first obtained. $IC_{50}$ measures the effectiveness of a compound or the concentration at which a compound/drug inhibits by half the biological or biochemical process. Mainly it measures the inhibition rate as a function of compound concentration and the results are plotted on a graph. To determine the $IC_{50}$, the data was fitted with the Hill-Slope model:

$$y = y_{top} \times \frac{y_{top} - y_{bottom}}{1 + (x/IC_{50})^{slope}}$$

where y is the percent activity and x is the corresponding concentration. The corresponding concentration where the inhibition is at 50% represents the $IC_{50}$. In patch clamping measurements the inhibition percentage was determined from membrane potential measurement. A 100% inhibition corresponds to the saturation of the membrane potential. As serial dilutions of the compound was added, the membrane potential changes. These changes were recorded either by patch clamping or dielectric measurements, depending on the experiment run. All compounds were tested using the procedure described above.

Figure 6A:
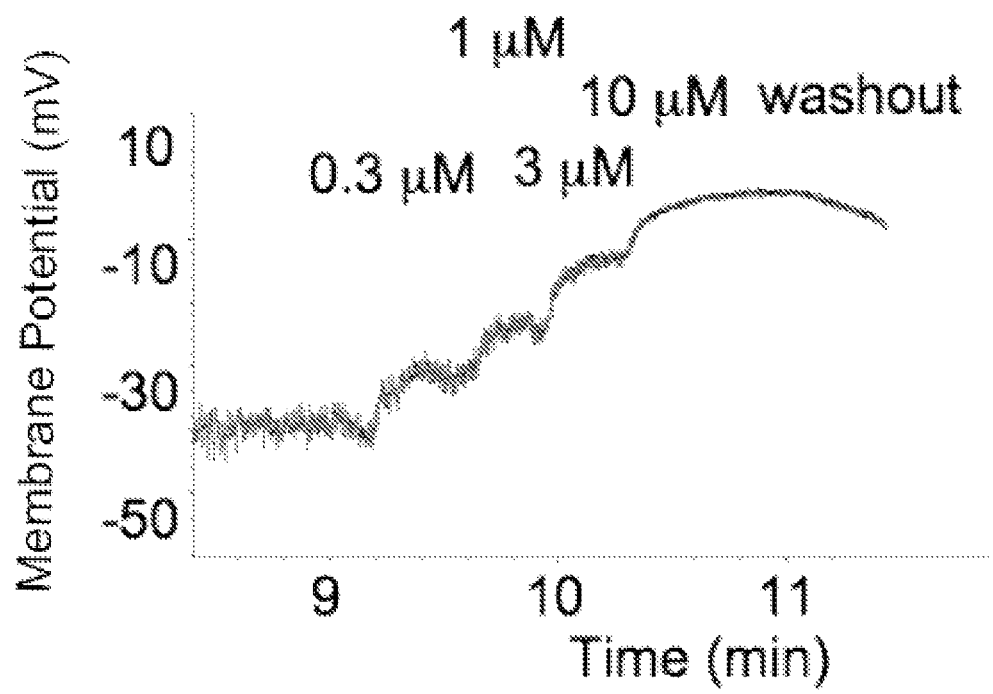
FIGS. 6(a)-6(b).
Figure 6B:
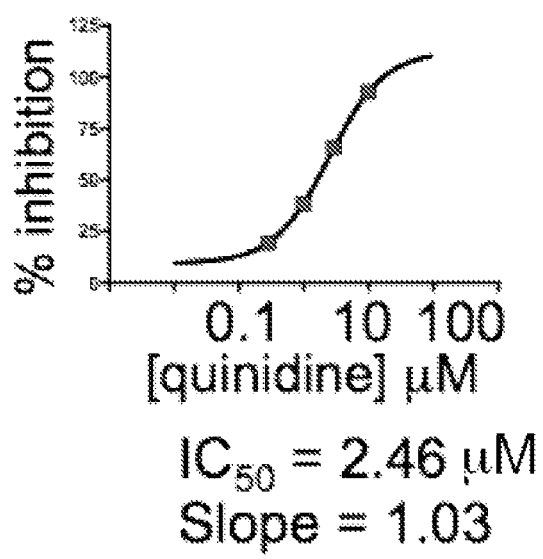

Quinidine is a class I antiarrhythmic drug, and its action on the hERG channels were studied by patch clamping and dielectric spectroscopy. The results from the patch clamping experiments are presented in FIG. 6(a). When no quinidine was present in the solution, the resting membrane potential was at −50 mV. By adding 1 μM quinidine, a part of the part of the potassium channels was blocked, the membrane potential dropped at −40 mV. Adding 3 μM quinidine blocked a larger number of potassium channels and the potential further dropped to −32 mV. At 30 μM, the membrane potential became −15 mV and remained unchanged with the increase of the quinidine concentration, indicating that 100% inhibition was reached. The corresponding $IC_{50}$ curve is shown in FIG. 6(b). The $IC_{50}$ value is 2.46 μM, meaning that it takes 2.46 μM of quinidine to reduce the activity of the hERG channels to half.

Figure 7A:
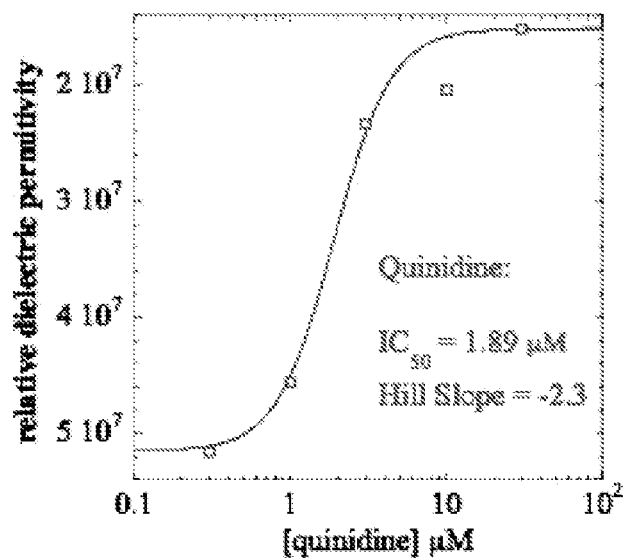
FIGS. 7(a)-7(c). $IC_{50}$ curve for quinidine obtained by dielectric spectroscopy.

FIG. 7(a) presents the $IC_{50}$ curve for quinidine obtained by dielectric spectroscopy. On the y axis the value of dielectric permittivity is plotted and on x the corresponding concentration. The concentrations tested were 0.3 μM, 1 μM, 3 μM, 10 μM and 30 μM, which are the same concentrations tested using the patch clamp method. The value of the $IC_{50}$ obtained this way is 1.89 μM which is very similar with the one obtained by patch clamping.

Figure 7B:
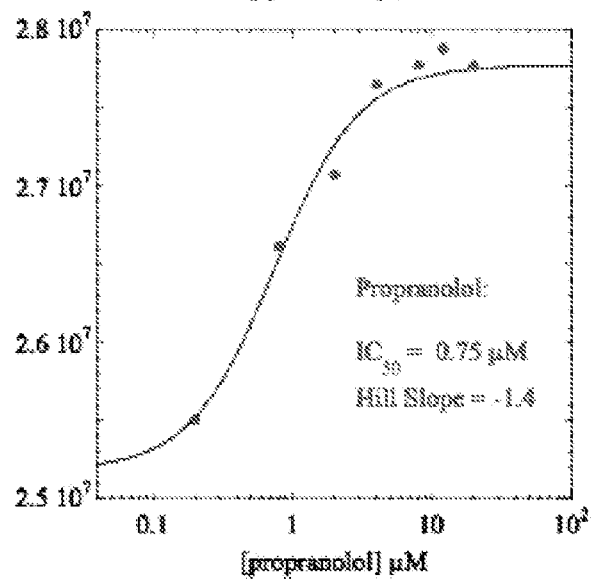

Propranolol is a class II antiarrhythmic drug also known as beta blocker. To obtain the $IC_{50}$ curve by dielectric spectroscopy, five concentrations spanning three orders of magnitude were tested, see FIG. 7(b). The smallest concentration, 0.2 μM induced only a small change of the dielectric response while a slightly higher concentration, 0.7 μM induced a large changes. From 4 μM and up there is no change in the dielectric response. The $IC_{50}$ obtained this way is 0.75 μM in good agreement with the one published in literature and obtained by patch clamping.

Figure 7C:
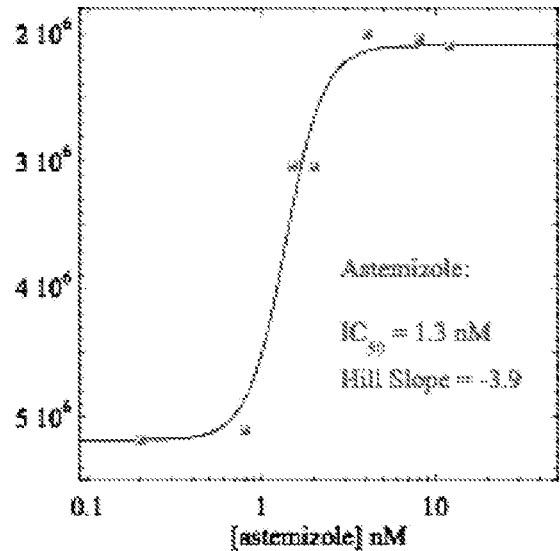

To obtain the $IC_{50}$ curve for astemizole by dielectric spectroscopy, five concentrations spanning three orders of magnitude were tested, see FIG. 7(c). Only a small change in the dielectric response is induced at 0.7 μM. The $IC_{50}$ obtained this way is 1.3 nM.

Many variations of the present invention will suggest themselves to those skilled in the art in light of the above detailed description. All such obvious variations are within the fully intended scope of the appended claims.

Those of skill in the art should, in light of the present disclosure, appreciate that many changes can be made in the specific embodiments where are disclosed herein and still obtain a like or similar result without departing from the spirit and scope of the invention.

The above mentioned patents, applications, test methods, publications are hereby incorporated by reference their entirety.

What is claimed is:

1. A method for measuring a change in membrane potential in a mammalian cell having an ion channel, said method comprising:
   (a) measuring the resting impedance in the alpha dispersion frequency range of a mammalian cell having the ion channel;
   (b) exposing a mammalian cell having the ion channel of the cell of step (a) to a test agent;
   (c) measuring the impedance in the alpha dispersion frequency range of the cell of step (b); and
   (d) calculating the change in the membrane potential of the cell upon exposure to the test agent, wherein calculating comprises:
      (i) determining the shape of the cell; and
      (ii) determining the change in the membrane potential based on fitting the measured impedance with the theoretical model:

$$\varepsilon_{sus}(\omega) = \varepsilon_0^* \left(1 + \frac{p\alpha(\omega)}{1 - p\alpha(\omega)/3}\right),$$

$$\text{with } \bar{\alpha}(\omega) = \frac{1}{VE_0} \int_V dV \frac{\varepsilon^* - \varepsilon_0^*}{\varepsilon_0^*} \langle \bar{E}(\omega) \rangle,$$

wherein
$\in_0^*$ is the complex dielectric function of the medium,
p is the volume concentration of the solution,
$\alpha(\omega)$ is the frequency dependent polarizability,
V is the volume,
$E_0$ electric field of amplitude
$\in^*$ is the non-uniform complex dielectric function of the composite particle, and
$\bar{E}(\omega)$ is the electric field inside the particle.

2. A method for measuring change in membrane potential in a cell containing a hERG ion channel comprising:
   (a) measuring the impedance of a mammalian cell having an ion channel in the alpha dispersion frequency range within a chamber;
   (b) combining a test agent and the mammalian cell having an ion channel;
   (c) measuring the impedance of the combination from step (b) in the alpha dispersion frequency range; and
   (d) calculating the change in the membrane potential of the cell, wherein calculating comprises:
   determining the change in the membrane potential based on fitting the measured impedance with the theoretical model wherein:

$$\varepsilon_{sus}(\omega) = \varepsilon_0^* \left(1 + \frac{p\alpha(\omega)}{1 - p\alpha(\omega)/3}\right),$$

$$\text{with } \bar{\alpha}(\omega) = \frac{1}{VE_0} \int_V dV \frac{\varepsilon^* - \varepsilon_0^*}{\varepsilon_0^*} \langle \bar{E}(\omega) \rangle,$$

wherein $\alpha(\omega)$ is defined for a spherical shape, wherein:

$$\alpha(\omega) = \frac{6\lambda_1}{3 - \lambda_1} \left[1 - \frac{2R\gamma/D}{\left(1 + j\omega\frac{R^2}{2D}\right)(3 - \lambda_1)(\tilde{\varepsilon}_1^* + \varepsilon_0^*) + 2R\gamma/D}\right],$$

wherein
$\in_0^*$ is the complex dielectric function of the medium,
p is the volume concentration of the solution,
$\alpha(\omega)$ is the frequency dependent polarizability,
V is the volume,
$E_0$ electric field of amplitude
$\in^*$ is the non-uniform complex dielectric function of the composite particle, and
$\bar{E}(\omega)$ is the electric field inside the particle,
wherein the membrane potential $\Delta V_0$ is defined by the ratio $\gamma/D$.

3. A method of screening a library of compounds for a channel modulator comprising:
   (a) measuring the resting impedance in the alpha dispersion frequency range of a mammalian cell having the ion channel;
   (b) exposing a mammalian cell having the ion channel of the cell of step (a) to a test agent;
   (c) measuring the impedance in the alpha dispersion frequency range of the cell of step (b); and
   (d) calculating the change in the membrane potential of the cell upon exposure to the test agent, wherein calculating comprises:
      (i) determining the shape of the cell; and
      (ii) determining the change in the membrane potential based on fitting the measured impedance with the theoretical model wherein:

$$\varepsilon_{sus}(\omega) = \varepsilon_0^* \left(1 + \frac{p\alpha(\omega)}{1 - p\alpha(\omega)/3}\right),$$

$$\text{with } \bar{\alpha}(\omega) = \frac{1}{VE_0} \int_V dV \frac{\varepsilon^* - \varepsilon_0^*}{\varepsilon_0^*} \langle \bar{E}(\omega) \rangle,$$

wherein
$\in_0^*$ is the complex dielectric function of the medium,
p is the volume concentration of the solution,
$\alpha(\omega)$ is the frequency dependent polarizability,
V is the volume,
$E_0$ electric field of amplitude,
$\in^*$ is the non-uniform complex dielectric function of the composite particle, and
$\bar{E}(\omega)$ is the electric field inside the particle.

4. The method of claim 1, 2, or 3, wherein a polarization effect is removed from the impedance data.

5. The method of claim 1, 2, or 3, wherein the cell is placed in a microfluidic system and flowed through a chamber.

6. The method of claim 1, 2, or 3, wherein the mammalian cell used to measure the resting impedance is a different cell than the cell used to measure the impedance of the cell exposed to the test agent.

7. The method of claim 1, 2, or 3, wherein the mammalian cell used to measure the resting impedance is the same cell used to measure the impedance of the cell exposed to the test agent.

8. The method of claim 1, 2, or 3, wherein the cell is exposed to at least one different concentration of test agent and at least one additional impedance measurement is subsequently obtained.

9. The method of claim 1, 2, or 3, further comprising washing out the test agent, adding a second test agent, and measuring the impedance in the alpha dispersion frequency range of the cell after exposure to the second test agent.

10. The method of claim 1, 2, or 3, wherein each impedance measurement is obtained from 1 Hz to 10 KHz.

11. The method of claim 1, 2, or 3, wherein each impedance measurement is obtained from 100 to 1000 Hz.

12. The method of claim 1, 2, or 3, further comprising accepting or rejecting or accepting the test agent based on the calculated change in membrane potential.

13. The method of claim 1, 2, or 3, wherein the ion channel is a hERG channel.

14. The method of claim 1, 2, or 3, further comprising the step of adding an ion channel antagonist after measuring the cell's resting impedance.

15. The method of claim 14, wherein the ion channel antagonist is quinidine.

16. The method of claim 1, 2, or 3, wherein a plurality of cells are measured simultaneously.

17. The method of claim 1, 2, or 3, wherein the test agent is a modulator of ion channel activity.

18. The method of claim 17, further comprising the step of calculating the IC50 value of the test agent.

19. The method of claim 1, 2, or 3, wherein the cell is a mammalian cell containing a hERG ion channel.

20. The method of claim 1, 2, or 3, wherein the ion channel has a resting potential of less than 0 V.

21. A method of selecting a modulator of an ion channel comprising:
    (a) placing a mammalian cell containing an ion channel in a chamber having two electrodes;
    (b) measuring the resting impedance in the alpha dispersion frequency range of a mammalian cell having the ion channel;
    (c) exposing a mammalian cell having the ion channel of the cell of step (b) to a test agent;
    (d) measuring the impedance in the alpha dispersion frequency range of the cell of step (c); and
    (e) calculating the change in the membrane potential of the cell upon exposure to the test agent, wherein calculating comprises:
        (i) determining the shape of the cell; and
        (ii) determining the change in membrane potential based on fitting the measured impedance with the theoretical model wherein:

$$\varepsilon_{sus}(\omega) = \varepsilon_0^* \left(1 + \frac{p\alpha(\omega)}{1 - p\alpha(\omega)/3}\right),$$

with $\overline{\alpha}(\omega) = \frac{1}{VE_0} \int_V dV \frac{\varepsilon^* - \varepsilon_0^*}{\varepsilon_0^*} \langle \overline{E}(\omega) \rangle,$ wherein
$\in_0^*$ is the complex dielectric function of the medium,
p is the volume concentration of the solution,
$\alpha(\omega)$ is the frequency dependent polarizability,
V is the volume,
$\overline{E}_0$ electric field of amplitude
$\in^*$ is the non-uniform complex dielectric function of the composite particle, and
$\overline{E}(\omega)$ is the electric field inside the particle,
wherein said test agent is selected as a modulator of an ion channel if said agent changes the membrane potential.

22. A high-throughput screening system comprising:
    a plurality of chambers having two electrodes in each of the plurality of chambers, wherein the electrodes are configured to applies a series of electric fields to cells within the chambers;
    a means for flowing solutions or suspensions containing mammalian cells containing an ion channel into and out of the chamber;
    a dielectric spectrometer configured to obtain impedance measurements in the alpha dispersion region;
    a data processing unit configured to calculating the membrane potential from impedance data, wherein calculating comprises:
    determining the shape of the cell,
    determining the membrane potential based on fitting the measured impedance with the theoretical model wherein:

$$\varepsilon_{sus}(\omega) = \varepsilon_0^* \left(1 + \frac{p\alpha(\omega)}{1 - p\alpha(\omega)/3}\right),$$

with $\overline{\alpha}(\omega) = \frac{1}{VE_0} \int_V dV \frac{\varepsilon^* - \varepsilon_0^*}{\varepsilon_0^*} \langle \overline{E}(\omega) \rangle,$ wherein
$\in_0^*$ is the complex dielectric function of the medium,
p is the volume concentration of the solution,
$\alpha(\omega)$ is the frequency dependent polarizability,
V is the volume,
$\overline{E}_0$ electric field of amplitude,
$\in^*$ is the non-uniform complex dielectric function of the composite particle, and
$\overline{E}(\omega)$ is the electric field inside the particle.

* * * * *